(12) United States Patent
Yang et al.

(10) Patent No.: US 7,901,462 B2
(45) Date of Patent: Mar. 8, 2011

(54) IMPLANTS WITH TEXTURED SURFACE AND METHODS FOR PRODUCING THE SAME

(75) Inventors: Xiaofan Yang, Warsaw, IN (US); Panjian Li, Fort Wayne, IN (US); Todd Smith, Fort Wayne, IN (US)

(73) Assignee: Depuy Products, Inc., Warsaw, IN (US)

( * ) Notice: Subject to any disclaimer, the term of this patent is extended or adjusted under 35 U.S.C. 154(b) by 0 days.

(21) Appl. No.: 11/165,209

(22) Filed: Jun. 23, 2005

(65) Prior Publication Data

US 2006/0293758 A1    Dec. 28, 2006

(51) Int. Cl.
*A61F 2/02* (2006.01)

(52) U.S. Cl. .................................................. 623/23.76

(58) Field of Classification Search ............... 623/1.39, 623/1.46, 23.5, 23.55, 23.57, 23.6; 427/2.24–2.27, 427/307, 309, 327
See application file for complete search history.

(56) References Cited

U.S. PATENT DOCUMENTS

| | | | | |
|---|---|---|---|---|
| 2,711,364 A * | 6/1955 | Beach | ............................ | 216/109 |
| 2,981,610 A * | 4/1961 | Snyder et al. | ................. | 252/79.3 |
| 3,106,499 A * | 10/1963 | Kendall | ........................ | 216/104 |
| 3,844,859 A * | 10/1974 | Roni | ............................. | 216/109 |
| 3,855,638 A * | 12/1974 | Pilliar | ........................ | 623/23.55 |
| 3,960,741 A * | 6/1976 | Gabrail | ........................ | 252/79.3 |
| 4,094,679 A | 6/1978 | Washizawa et al. | | |
| 4,314,876 A * | 2/1982 | Kremer et al. | ................. | 216/109 |
| 4,550,448 A * | 11/1985 | Kenna | ........................... | 623/23.6 |
| 4,554,050 A * | 11/1985 | Minford et al. | ............... | 216/108 |
| 4,818,559 A | 4/1989 | Hama et al. | | |
| 5,236,459 A * | 8/1993 | Koch et al. | ...................... | 606/62 |
| 5,258,098 A | 11/1993 | Wagner et al. | | |
| 5,307,594 A * | 5/1994 | Panchison | ...................... | 451/29 |
| 5,376,236 A * | 12/1994 | Hanson et al. | ................. | 216/108 |
| 5,439,569 A * | 8/1995 | Carpio | ............................ | 134/1.3 |
| 5,456,723 A * | 10/1995 | Steinemann et al. | ...... | 623/23.53 |
| 5,545,262 A * | 8/1996 | Hardee et al. | ................. | 148/527 |
| 5,571,188 A * | 11/1996 | Ellingsen et al. | ............ | 427/2.26 |
| 5,607,480 A * | 3/1997 | Beaty | ............................ | 623/23.5 |
| 5,705,082 A | 1/1998 | Hinson | | |

(Continued)

FOREIGN PATENT DOCUMENTS

WO        WO 0166479 A1 *    9/2001

(Continued)

OTHER PUBLICATIONS

Brady et al., "Chemistry: The Study of Matter and its Changes", 1993, pp. 706-707, John Wiley & Sons, Inc.*

(Continued)

*Primary Examiner* — William H. Matthews

(74) *Attorney, Agent, or Firm* — Nutter McClennen & Fish LLP

(57) ABSTRACT

Compositions and methods are provided for preparing a metal substrate having a uniform textured surface with a plurality of indentations with a diameter in the nanometer and micrometer range. The textured surface is produced by exposing the substrate to an etching fluid comprising a hydrogen halide acid and/or an oxyacid, a chloride containing compound, and an oxidizing agent. The etching solution can be used at ambient temperature without damaging the metal elements on the substrate surface. This textured surface enhances adherence of coatings or cells onto the textured surface, improves the retention of proteins on the surface, and encourages bone in-growth.

27 Claims, 8 Drawing Sheets

U.S. PATENT DOCUMENTS

| | | | |
|---|---|---|---|
| 5,826,586 A * | 10/1998 | Mishra et al. | 128/898 |
| 5,843,172 A * | 12/1998 | Yan | 623/1.42 |
| 5,843,289 A * | 12/1998 | Lee et al. | 204/192.3 |
| 5,846,374 A * | 12/1998 | Parab et al. | 156/345.11 |
| 5,855,612 A | 1/1999 | Ohthuki et al. | |
| 5,876,453 A * | 3/1999 | Beaty | 433/201.1 |
| 5,986,169 A | 11/1999 | Gjunter | |
| 6,033,582 A | 3/2000 | Lee et al. | |
| 6,069,295 A * | 5/2000 | Leitao | 623/11.11 |
| 6,096,140 A | 8/2000 | Susa et al. | |
| 6,136,369 A * | 10/2000 | Leitao et al. | 427/2.27 |
| 6,143,948 A * | 11/2000 | Leitao et al. | 424/422 |
| 6,146,686 A * | 11/2000 | Leitao | 427/2.27 |
| 6,183,255 B1 * | 2/2001 | Oshida | 433/201.1 |
| 6,207,218 B1 * | 3/2001 | Layrolle et al. | 427/2.27 |
| 6,261,322 B1 * | 7/2001 | Despres et al. | 623/23.53 |
| 6,319,286 B1 * | 11/2001 | Fernandez et al. | 623/23.18 |
| 6,491,723 B1 | 12/2002 | Beaty | |
| 6,582,470 B1 * | 6/2003 | Lee et al. | 623/23.55 |
| 7,048,870 B1 * | 5/2006 | Ellingsen et al. | 216/109 |
| 7,386,065 B2 * | 6/2008 | Tu et al. | 375/334 |
| 7,501,073 B2 * | 3/2009 | Wen et al. | 216/109 |
| 2003/0065401 A1 | 4/2003 | Amrich et al. | |
| 2003/0108659 A1 | 6/2003 | Bales et al. | |
| 2003/0130736 A1 | 7/2003 | Raab | |
| 2004/0121290 A1 | 6/2004 | Minevski et al. | |
| 2004/0167632 A1 | 8/2004 | Wen et al. | |
| 2004/0199242 A1 * | 10/2004 | Hong et al. | 623/1.16 |
| 2005/0049716 A1 | 3/2005 | Wagener et al. | |
| 2005/0070989 A1 * | 3/2005 | Lye et al. | 623/1.4 |
| 2005/0112397 A1 * | 5/2005 | Rolfe et al. | 428/593 |

FOREIGN PATENT DOCUMENTS

| | | | |
|---|---|---|---|
| WO | WO 02/060507 A | | 8/2002 |
| WO | WO 03008657 A1 * | | 1/2003 |
| WO | WO 2004008984 A1 * | | 1/2004 |

OTHER PUBLICATIONS

CRC Handbook of Metal Etchants, CRC Press, Boston, 315-316 (1991).

Ferrari, M. et al., "Evaluation of a Chemical Etching Solution for Nickel-Chromium-Beryllium and Chromium-Cobalt Alloys," J. Prosthetic Dentistry 62(5):516 (1989).

Jokela-Hietamaki, M. et al., "Resin Bond to Electrolytically Etched Cobalt-Chromium Alloys," Scandinavian J. Dental Res. 95(1):82 (1987).

Liu, L. et al., "Etched Casting Resin Bonded Bridge: The Laboratory Study of Electrolytic Etching of a Co-Cr Alloy," Chinese Oral Med. J. 22(5):287 (Chinese, English @ 311)(1987).

Nabadalung, D. et al., "Effectiveness of Adhesive Systems for a Co-Cr Removable Partial Denture Alloy," J. Prosthodontics 7(1):17 (1998).

Petzow, G. et al., Metallographic Etching, Am. Soc. for Metals, Ohio, 51 (1978).

Reclaru, L. et al., "Cobalt-Chromium Dental Alloys Enriched with Precious Metals," European Cells & Materials 7(Supp.2):51 (2004).

Sarac, Y. et al., "The Effects of Different Metal Surface Treatments on Marginal Microleakage in Resin-Bonded Restorations," Tr. J. of Medical Sciences 28:685 (1998).

Ferrari, M. et al., "Evaluation of a Chemical Etching Solution for Nickel-Chromium-Beryllium and Chromium-Cobalt Alloys," J. Prosthetic Dentistry 62(5):516-521 (1989).

Mendelson, S. et al., "Dislocation Etch Pit Formation in Sodium Chloride," J. Applied Physics 32(8):1579-1583 (1961).

Wolf, S. et al., "Photoresist Removal," Silicon Processing for the VLSI Era (Lattice Press) 1:518 (1986).

European Search Report, from related EP 06252704.9, dated Jul. 28, 2006.

European Search Report, from related EP 06252690.0, dated Jul. 28, 2006.

Liu, X. et al., "Surface Modification of Titanium, Titanium Alloys, and Related Materials for Biomedical Applications," Mat. Sci. & Eng. R. 47:49-121 (2004).

Catledge, S. et al., "Nanostructured Ceramics for Biomedical Implants," J. Nanoscience & Tech. 2(3):1-20 (2002).

Kern, W., "Handbook of Semiconductor Wafer Cleaning Technology," William Andrew Publ. 120-128 (1993).

* cited by examiner

A

B

C

D

A

B

C

D

A

B

C

D

IMPLANTS WITH TEXTURED SURFACE AND METHODS FOR PRODUCING THE SAME

FIELD OF THE INVENTION

The invention relates to orthopaedic implants and to methods and compositions for preparing such implants with a textured surface.

BACKGROUND OF THE INVENTION

The effectiveness of an orthopaedic implant often depends upon the presence of an irregular surface on the implant, into which the bone may grow to create a natural joinder between the bone and the implant. Several techniques have been used to create implants with irregular surfaces. Grit blasting is one surface roughening technique, but grit blasting can cause significant changes to the surface topography by damaging the metal elements (e.g., beads) on the surface layer of the substrate. Other mechanical roughening techniques, such as scratching or burr grinding, have also been used. These techniques can also present drawbacks, including distortion of the substrate, removal of excess material, inability or difficulty to roughen certain surfaces, and inconsistent surface roughening.

Electrochemical or chemical etching techniques have also been used to roughen the surface of an implant. Chemical etching often involves using toxic reagents, such as methanol, or a strong acid at a high temperature (as high as 80° C., for example), or strong acid mixtures. Chemical etching, even under these stringent conditions, can require several hours to several days to roughen a surface. Chemical etching also presents the potential for preferential etching on grain boundaries, which can reduce the mechanical properties of the implants Furthermore, the surface roughening of certain implants made with a cobalt-chromium alloy can be difficult because of the corrosion resistance of chromium.

Accordingly, there remains a need for improved and reliable methods to form an effective textured surface on a metal or metal alloy substrate. There is also a need for orthopaedic implants having a surface texture.

SUMMARY OF THE INVENTION

The present invention provides methods and compositions for preparing a substrate with a textured surface. The textured surface can be produced by exposing the surface of the implant to a relatively mild etching solution comprising a hydrogen halide acid or a mixture of a hydrogen halide acid and an oxyacid (also known as "oxoacid"), a chlorine containing compound, and oxidizing agent. The etching solution may optionally contain a phosphate containing compound as well. The substrate need only be exposed to the etching solution for a relatively short period of time to cause nanometer and micrometer sized indentations. This textured surface enhances adherence of non-metallic coatings or cells onto the textured surface, improves the retention of proteins on the surface when contacted with biological fluids, and encourages bone in-growth. The methods and compositions are useful for producing a uniform textured surface on hard metals such as cobalt and its alloys, especially cobalt chromium alloy.

A further advantage of the etching process of the invention is that it avoids the use of a hot mixture of methanol and acid, which produces potentially harmful vapors that present waste and disposal issues, or the use of a concentrated acid mix such as HCl and $HNO_3$ mix, which is dangerous because of its corrosive properties. The etching process can also be conducted at room temperatures and for shorter durations of time.

In one aspect, the invention pertains to a chromium-containing biomedical implant comprising a textured surface with a plurality of pores or indentations. The indentations, which have a diameter in the range of about 200 nanometers to 15 micrometers, promote enhanced bone in-growth and attachment of a non-metallic coating or a cell to the textured surface. The chromium-containing implant can be any biocompatible metal alloy that contains chromium, such as cobalt-chromium. The textured surface of the implant can also be coated, after etching, with a non-metallic coating such as a bioceramic coating.

In another aspect, the invention pertains to a chromium-containing biomedical implant comprising a textured surface with a plurality of indentations. The textured surface is produced by an etching solution comprising hydrochloric acid at a concentration in the range of about 1M to 12M, phosphoric acid, if present, at a concentration in the range of about 0.01M to 14M, a chlorine containing compound, if present, at a concentration in the range of about 0.01M to 2M, a phosphate containing compound, if present, at a concentration in the range of about 0.01M to 0.4M, and an oxidant at a concentration in the range of about 0.01M to 10M. The indentations have a diameter in the range of about 200 nanometers to 15 micrometers.

In another aspect, the invention pertains to an etching fluid, and a method of a etching, in which the etching fluid comprising an acid selected from the group consisting of a hydrogen halide acid, and a mixture of a hydrogen halide acid and an oxyacid. The hydrogen halide acid has a concentration range of about 1M to 12M, and the oxyacid has a concentration range of about 0.01M to 14M. The etching fluid also comprises a chlorine containing compound at a concentration in the range of about 0.01M to 2M, and an oxidant at a concentration in the range of about 0.01M to 10M. The etching solution produces a substantially uniform textured surface on a chromium containing biomedical implant, and the textured surface has a plurality of indentations having a diameter in the range of about 200 nanometers to 15 micrometers. The etching fluid may further comprise a phosphate containing compound.

In yet another aspect, the invention pertains to an etching fluid comprising hydrochloric acid at a concentration in the range of about 1M to 12M, a phosphoric acid at a concentration in the range of about 0.01M to 14M, a chlorine containing compound at a concentration in the range of about 0.01M to 2M, a phosphate containing compound at a concentration in the range of about 0.01M to 0.4M, and an oxidant at a concentration in the range of about 0.01M to 10M. The etching solution produces a uniform textured surface on a substrate that promotes attachment of a non-metallic surface coating or a cell. Such a textured surface also enhances bone in-growth. The etching fluid creates a substantially uniform surface texture in a chromium containing biomedical implant under etching conditions conducted at a temperature in the range of about 10° C. to about 100° C.

In yet another aspect, the invention pertains to a method of producing a biomedical implant with a textured surface comprising exposing at least a portion of a chromium containing implant to an etching fluid. The implant can be incubated with the etching fluid at a temperature range of about 10° C. to about 100° C. until the implant contains a plurality of uniformly distributed indentations in the exposed portion of the implant. The textured surface with a plurality of indentations can be produced upon a smooth metal surface or a surface with metallic elements.

DETAILED DESCRIPTION OF THE INVENTION

Figure 1:
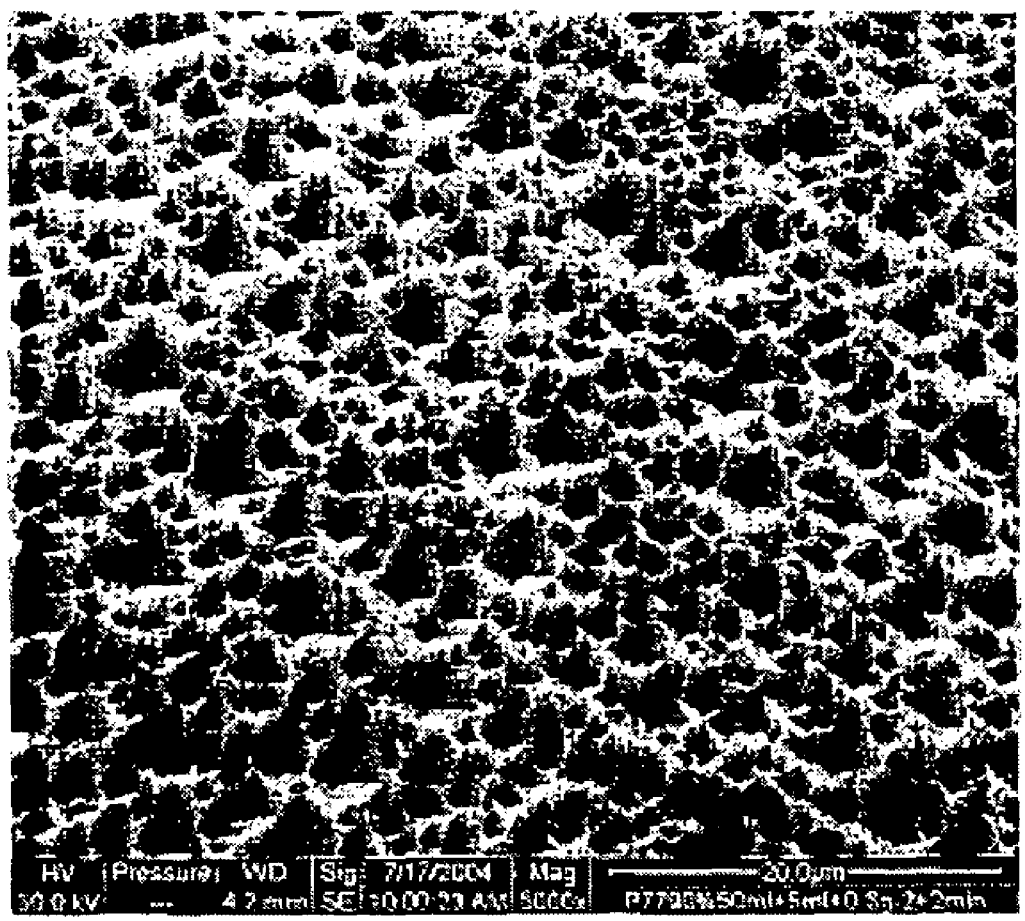
FIG. 1 is an SEM micrograph of an etched surface of a cobalt-chromium porous coated sample at a 5000× magnification which has been etched for four minutes at room temperature in accordance with one embodiment of the invention.

Certain exemplary embodiments of the invention will now be described to provide an overall understanding of the principles of the structure, function, manufacture, and use of the methods and compositions disclosed herein. Those skilled in the art will understand that the methods and compositions specifically described herein are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The invention provides a biomedical implant, e.g., an orthopaedic implant, that has at least on a portion thereof, a textured surface formed of a plurality of discrete indentations, e.g., pores. The pores of the textured surface can be in the nanometer to micron size range in both diameter and depth. The pores can have a diameter in the range of about 100 nanometers to 15 micrometers. In other embodiments, the pore size is in the range of about 200 nanometers to 5000 nanometers, or in the range of about 300 nanometers to 3000 nanometers, or in the range of about 300 nanometers to 1000 nanometers. The depths of the pores may vary; typically, the depths of the pores range up to about 2.4 microns, and, for example, can be in the range of about 0.8 microns to 2.4 microns, in the range of about 1.0 microns to 2.0 microns, in the range of about 1.2 microns to 1.8 microns, or in the range of about 1.4 microns to 1.6 microns.

In a further aspect, the implant is etched after having applied thereto a porous coating of metallic elements, such as metallic beads. After etching, the implant has a substantially uniform distribution of metallic elements across the entire surface of the implant upon which the textured surface is formed. That is, etching is able to occur three dimensionally such that the distribution of pores formed by the etching extends in all geometrical spatial dimensions. For example, etching and pore formation can occur such that pores are formed on irregular and undercut surfaces, as well as on smooth or flat portions. Each pore is a substantially discrete cavity formed in the surface of the implant. Adjacent pores are separated by a wall or projection that extends from the base of the pore. The walls of the projections may be of any shape, including columnar and irregular shaped. The textured surface with its minute indentations, deformations and/or raised portions is an opaque surface, slightly rough to the touch.

The biomedical implant upon which an etched surface can be formed can be any metal that has high mechanical strength, durability and biocompatibility. The mechanical properties of the implant should be those required for its intended use. In one embodiment, the metal is cobalt or its alloy containing chromium. Cobalt alloys can be created with one or more alloying elements such as carbon, chromium, iron, manganese, nickel, silicon, manganese, nitrogen and molybdenum. In one embodiment, the metal alloy is a cobalt-chromium alloy of the ASTM type F-75 (Standard Specification for Cobalt—28 Chromium—6 Molybdenum Alloy Castings and Casting Alloy for Surgical Implants, UNS R30075, Designation F75-01). In another embodiment, the metal alloy is a cobalt-chromium alloy of the ASTM type F-1537 (Standard Specification for Wrought Cobalt—28Chromium—6 Molybdenum Alloys for Surgical Implants, UNS R31537, UNS R31538, and UNS R31539, Designation F1537-00). Exemplary materials typically contain chromium at about 26-30%, molybdenum at about 5-7%, and a balance of cobalt. Another example of a chromium-containing alloy that can be used is stainless steel. In addition to chromium-containing alloys, other examples of metals that can be used are those which are stable in the body, and include, but are not limited to, titanium and titanium alloys. One skilled in the art will appreciate that the implant can assume any shape that is required for its intended application.

The biomedical implant upon which an etched surface can be formed can be a metal body that has a coating of metallic elements adhered to at least a portion of the outer surface of the metal body. The metallic elements may form a three-dimensional porous surface geometry on the surface of the metallic biomedical implant. At least a portion of the metallic elements are interconnected to form pores between adjacent metallic elements (i.e. interstitial pores). These interstitial pores can range in size from about 10 microns to about 200 microns, and in some cases up to 750 microns. Such implants with coatings of metallic elements are referred to herein as "porous coated," and the coating of metallic elements is referred to as a "porous coating."

The metallic elements forming the porous coating can be provided in any suitable form. Generally, the metallic elements comprise metallic particles, metallic fibers, metallic wires, or combinations thereof. The metallic elements can be arranged in a predetermined pattern. For instance, a plurality of metallic fibers or wires can be arranged to form a mesh, which can be adhered to the outer surface of the metal body. In a preferred embodiment, the metallic elements comprise metallic particles. More preferably, the metallic particles comprise substantially spherical metallic beads. These metallic particles or beads can be of any suitable size. Typically, the size of the metallic particles or metallic beads is from about 40 microns to several millimeters.

The metallic elements of the porous coating are interconnected to each other and to the outer surface of the metal by bridges of metal. As used herein, these interconnecting bridges are referred to as grain boundaries. These boundaries serve to adhere the metallic elements to each other and to the outer surface of the metal body. An implant with such a porous network with such grain boundaries and interstitial pores may be made in any suitable manner. One suitable method is described in U.S. Pat. No. 3,855,638 and U.S. Patent Application No. 2004/0167632. In this method, a plurality of metallic elements are coated on the outer surface of the metal body, and then the implant is sintered to fuse the metallic elements to the body of the implant and to each other. The fusion of the metallic elements during the sintering process creates the boundaries between the metallic elements of the porous coating and between the outer surface of the metal boundary and the metallic elements of the porous coating. The sintering process preserves interstitial spaces or pores between the metallic elements. Typically, this method yields a metallic implant with interstitial pore sizes of greater than 20 microns.

The textured surface features of the implant provides an increased surface area. Further increases in the surface area can be provided by uniform textured surface features. Such increases in surface area can improve the adherence of any non-metallic coating applied to the substrate, and it can also enhance the biological fixation of the implant due, for example, to enhanced bone in-growth. Examples of suitable non-metallic coatings that can be applied to the substrate include, but are not limited to, hydroxyapatite, alumina, zirconia, titanium nitride and boron nitride. In another embodiment, the implant surface can be exposed to cells, or a population of cells such that the cells attach and adhere to the plurality of uniform raised portions and indentations. The attached cells can then proliferate and grow on the surface and encourage cell in-growth onto and into the implant. Examples of cells that can be used include, but are not limited to, chondroctyes, osteoblasts, and osteoclasts.

In yet another embodiment, the implant surface can be exposed to growth factors or proteins that enhance cell adhesion and cell growth. Suitable proteins include, but are not limited to, collagen, fibronectin, vitronectin, laminin, osteopontin, SPARC (secreted protein acidic and rich in cysteine), and bone morphogenetic proteins (BMPs). Suitable growth factors include, but are not limited to, vascular endothelial growth factor (VEGF), platelet-derived growth factor (PDGF), insulin-like growth factor (IGF), basic fibroblast growth factor (bFGF), transforming growth factor beta (TGF-beta), and cartilage-derived growth factor (CDGF), hematopoetic growth factor (HGF), heparin binding growth factor, and the like.

In one embodiment, the etching fluid useful with the invention comprises an acid component selected from the group consisting of a hydrogen halide acid or a mixture of a hydrogen halide acid an oxyacid. The concentration of the hydrogen halide acid can be in the range of about 1M to 12M and the concentration of the oxyacid can be in the range of about 0.01M to 14M. The etching fluid also comprises a chlorine containing compound at a concentration in the range of about 0.01M to 12M; and an oxidant at a concentration in the range of about 0.01M to 10M. The etching solution may further comprise a phosphate containing compound at a concentration in the range of about 0.01M to 0.4M. It will be appreciated that the concentration of the acid component that is used depends on whether one or both of the hydrogen halide acid and an oxyacid are used with the etching solution, and the identity of the specific hydrogen halide acid and/or oxyacid that is used. For example, if both a hydrogen halide acid and an oxyacid are used, the concentrations of each will be relatively lower in comparison to if just one of the acids was used. By way of further example, if only hydrochloric acid is used, without phosphoric acid, then the concentration of hydrochloric acid can range from about 1M to about 12M. If, on the other hand, phosphoric acid is used together with hydrochloric acid, then the concentration of hydrochloric acid that can be used is in the range of about 3M to about 5M; for example, hydrochloric acid with a concentration of about 3.4M can be used if in a mixture with 4.9M phosphoric acid. It will be appreciated that the etching fluid need not include all of the components described above and shown in Example 1. Thus, in one embodiment, the etching fluid may comprise a hydrogen halide acid and an oxidant. In another embodiment, the etching fluid may comprise a hydrogen halide acid, an oxyacid, and an oxidant. In yet another embodiment, the etching fluid may comprise a hydrogen halide acid, an oxyacid, an oxidant and a chlorine containing compound and/or a phosphate containing compound.

The hydrogen halide acids are acids with a halogen group. Examples of hydrogen halide acids include, but are not limited to hydrogen fluoride, hydrogen chloride (hydrochloric acid), hydrogen bromide, and hydrogen iodide. In one embodiment, the hydrogen halide is hydrochloric acid at a concentration in the range of about 1M to 12M; about 3.5M to 8M; and about 4.6M.

Oxyacids have the general formula $H_aX_bO_c$, where "a" represents the number of hydrogen atoms, "X" represents an element other than hydrogen or oxygen, "b" represents the number of "x" atoms, and "c" represents the number of oxygen atoms. Examples of oxyacids include, but are not limited to, nitric acid, ($HNO_3$), sulfuric acid, ($H_2SO_4$), and phosphoric acid, ($H_3PO_4$). In one embodiment, the oxyacid is phosphorous containing acid at a concentration in the range of about 0.01M to 14M; about 4M to 8M; and about 5.6M. Examples of phosphorous-containing oxyacids include, but are not limited to, ortho-phosphoric acid ($H_3PO_4$), peroxomonophosphoric acid ($H_3PO_5$), diphosphoric acid ($H_4P_2O_7$), peroxodiphosphoric acid ($H_4P_2O_8$), triphosphoric acid ($H_5P_3O_{10}$), hypophosphoric acid ($H_4P_2O_6$), polyphosphoric acid ($H_{n+2}P_nO_{3n+1}$), where n is an integer up to 17, isohypophosphoric acid ($H_4P_2O_6$), cyclo-trimetaphosphoric acid (($HPO_3)_3$), phosphonic acid ($H_3PO_3$), cyclotetrametaphosphoric acid (($HPO_3)_4$), diphosphonic acid ($H_4P_2)_5$), polymetaphosphoric acid ($HPO_3)_n$, phosphinic acid ($H_3PO_2$), and anhydrous oxyacid.

A chlorine containing compound contains chlorine, which is typically present as a chloride. Most chlorides are salts that are formed either by direct union of chlorine with a metal or by reaction of hydrochloric acid (a water solution of hydrogen chloride) with a metal, a metal oxide, or an inorganic base. Examples of chlorine containing compounds include, but are not limited to, sodium chloride (NaCl), potassium chloride (KCl), calcium chloride ($CaCl_2$), ammonium chloride ($NH_4Cl$) and ferrous chloride ($FeCl_3$), or mixtures thereof. In one embodiment, the chlorine containing compound has a concentration in the range of about 0.01M to 2M; about 0.6M to 1.1M; and about 0.9M.

Phosphate containing compounds are minerals with a basic chemical unit of tetrahedral ($PO_4$) groups with the phosphorus atom at the center and oxygen atoms at each of the four corners. This chemical group can be combined with metal ions in a 1:1 ratio, or usually in more complex combinations, with other ions such as hydroxyl groups (OH), a halogen, or even water molecules. Examples of phosphate containing compounds include, but are not limited to, potassium phosphate ($K_2HPO_4$), sodium phosphate ($Na_2HPO_4$), and sodium dihydrogen phosphate ($NaH_2PO_4$), and mixtures thereof. The phosphate containing compound can be used at a concentration of 0.01M to 0.4M. For example, if the phosphate containing compound is sodium dihydrogen phosphate, the concentration can be in the range of about 0.01M to 0.35M. If the phosphate containing compound is disodium hydrogen phosphate, the concentration can be in the range of about 0.01M to 0.3M. It will be appreciated that all forms of phosphate containing compounds can be used which include, but are not limited to, mono, di-, tri-salts of the compound, e.g., sodium phosphate, disodium phosphate, trisodium phosphate, and the like.

An oxidant is a substance that oxidizes another substance. Chemical groups that act as oxidants include, but are not limited to, peroxides ($O_2^{-2}$), nitrates ($NO_3^-$), nitrites ($NO_2^-$), perchlorates ($ClO_4^-$), chlorates ($ClO_3^-$), chlorites ($ClO_2^-$), hypochlorites ($ClO^-$), dichromates ($Cr_2O_7^{-2}$), permanganates ($MnO_4^-$), and persulfates ($S_2O_8^{-2}$). Examples of oxidants include, but are not limited to, hydrogen peroxide, sodium peroxide, perchloric acid, ammonium persulphate. In one embodiment, the oxidant is hydrogen peroxide at a concentration in the range of about 0.32M to 10M; about 1M to 3.2M; and about 1.6M. In one embodiment, the hydrogen peroxide can be used at 1.6M concentration. In another embodiment, the oxidant is ammonium persulphate at a concentration in the range of about 0.01M to 1M; about 0.6M to 1.1M; and about 0.9M.

In one embodiment, the etching solution includes hydrochloric acid (HCl) at a concentration of about 4.6M, phosphoric acid ($H_3PO_4$) at a concentration of about 5.6M, ammonium chloride at a concentration of about 0.9M, sodium dihydrogen phosphate ($NaH_2PO_4$) at a concentration of about 0.01 to 0.35M and an oxidant, that can be hydrogen peroxide ($H_2O_2$) at a concentration of about 1.6M or ammonium persulphate ($(NH_4)_2S_2O_8$) at a concentration of about 0.33M In another aspect, the invention pertains to methods of producing a chromium-based biomedical implant comprising a textured surface with a plurality of indentations. The textured surface is produced by exposing the implant to an etching solution comprising a hydrogen halide acid at a concentration in the range of about 1M to 12M and/or an oxyacid at a concentration in the range of about 0.01M to 14M, a chlorine containing compound at a concentration in the range of about 0.01M to 2M, and an oxidant at a concentration in the range of about 0.01M to 10M. The etching solution can optionally contain other components, including a phosphate containing compound at a concentration in the range of about 0.01M to 0.4M. As noted above, the etching solution is effective to produce a uniform textured surface on a substrate with a plurality of indentations that can promote bone in-growth or the attachment of a non-metallic coating or a cell to the textured surface.

Before the etching process begins, the substrate surface can be cleaned using typical usual cleaning procedures, such as degreasing (e.g., either chemical, electrochemical or electrolytic). Alternatively, other chemical cleaning operations may be used, such as cleaning with an alkaline solution. The substrate surface may be degreased by ultrasonic cleaning in detergent, followed by ultrasonic cleaning in operating room water. The cleaned metal surface is then exposed to a suitable volume of etching solution in a container or bath. The volume of the etching solution depends on the surface area of the substrate for which etching is desired. In some instances, the entire surface of the implant will be etched, and thus the volume of the etching solution should be sufficient to cover the entire implant. In other applications, only a portion of the implant will be etched and only a desired portion of the implant need be exposed to the etching solution. One skilled in the art will readily appreciate the volume of etching solution that is required for a given etching procedure.

The etching procedure of the invention can be conducted at a range of temperatures. In exemplary embodiments, the temperature of the etching solution during the etching process can be maintained within the range of about 10° C.-100° C., and preferably in the range of about 20° C.-40° C. In one embodiment, the etching solution can be maintained at room temperature (i.e., about 20-25° C.) during the etching process.

One skilled in the art will also appreciate that etching can be conducted for a variable time period. In exemplary embodiments, the etching process can be carried out for a period of time within the range of about 1 to 60 minutes, preferably about 15 to 30 minutes. Following the etching process, the metal surface can be washed, as known in the art, to remove any residual etching fluid.

As noted above, the etching process of the invention results in uniformly distributed indentations over the exposed substrate surface without reducing the mechanical properties of the implant. Such uniform etching provides advantages over other, known etching techniques. For example, some etching techniques can result in preferential etching, which is primarily focused at an interface of surface geometries, or at the boundaries between the metallic elements of the porous coating. Preferential etching often results in a non-uniformly etched surface and can lead to compromised mechanical properties; for example, the boundaries between metallic elements of the porous coating can be degraded by preferential etching. The results shown below illustrate that porous coated samples having a rough, irregular surface texture can be etched according to the invention in such a way that a uniform distribution of pores is obtained on all etched surfaces, regardless of the surface geometry before etching. Thus, preferential etching at the boundaries or interface between beads of the samples is avoided and the mechanical properties of the sample are preserved. Accordingly, the etching process can be carried out on surfaces of various geometries, including internal or undercut surfaces, planar surfaces, and non-planar surfaces. The resulting textured surface provides a surface with enhanced bonding properties and/or properties for receipt of a non-metallic coating.

The mechanical properties of the implant can be tested using a shearing test by determining the implants ability to withstand a shear force applied to the surface thereof. For example, the mechanical properties of the metallic implant can be measured using any of the techniques for testing metallic coatings set forth in ASTM F1044-99 entitled, "Standard Test Method for Shear Testing of Calcium Phosphate Coatings and Metallic Coatings." For example, the mechanical properties implant is measured by embedding a portion of the metallic implant in a curable material (e.g., acrylic resin or polymer), and then applying a load to the implant in a direction intended to pull the implant from the body of the curable material. Typically, an implant which has been subjected to the chemical etching method of the invention can withstand a shear force of about 13,000 kPa (about 2,000 psi), about 20,000 kPa (about 3,000 psi), or about 27,000 kPa (about 4,000 psi) or more.

The following example is illustrative of the principles and practice of this invention. Numerous additional embodiments within the scope and spirit of the invention will become apparent to those skilled in the art.

EXAMPLE

Example 1

Preparation of a Textured Surfaces

This example demonstrates the preparation of a textured surface with a plurality of indentations using the etching fluid of the invention. All chemical reagents were obtained from Fischer Scientific. The samples used were cobalt-chromium substrates coated with POROCOAT® cobalt-chromium alloy beads, available from DePuy Orthopaedics, Inc. A portion of the each sample was exposed to an etching solution according to the present invention. The identity of each etching solution was evaluated, as well as the time of exposure to the etching solution at room temperature, are described in detail below in FIGS. 1-8.

FIG. 1 is an SEM micrograph of an etched surface of a cobalt-chromium porous coated sample at a 5000× magnification which has been etched for four minutes at room temperature in an etching solution having 9.8M HCl, 10 ml $H_2O$, 0.03M $FeCl_3$ and 2.9M $H_2O_2$.

Figure 2:
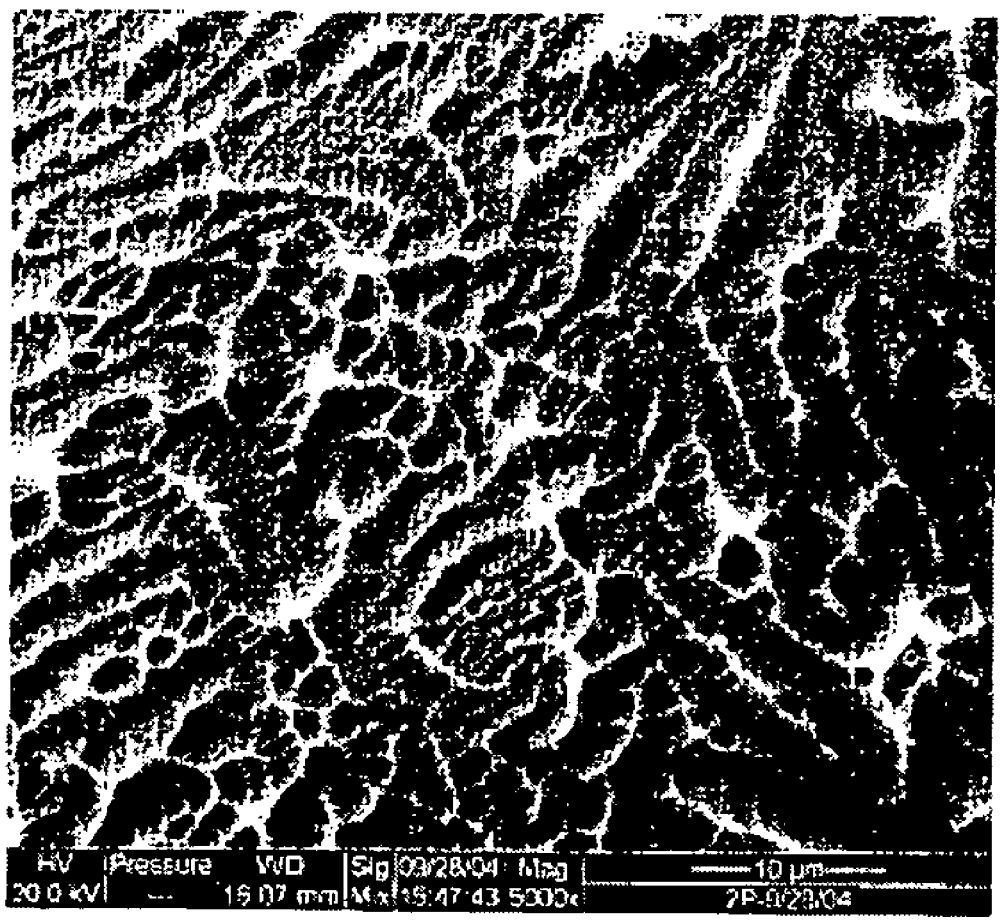
FIG. 2 is an SEM micrograph of an etched surface of a cobalt-chromium porous coated sample at a 5000× magnification which has been etched for 15 minutes at room temperature in accordance with one embodiment of the invention.
Figure 3:
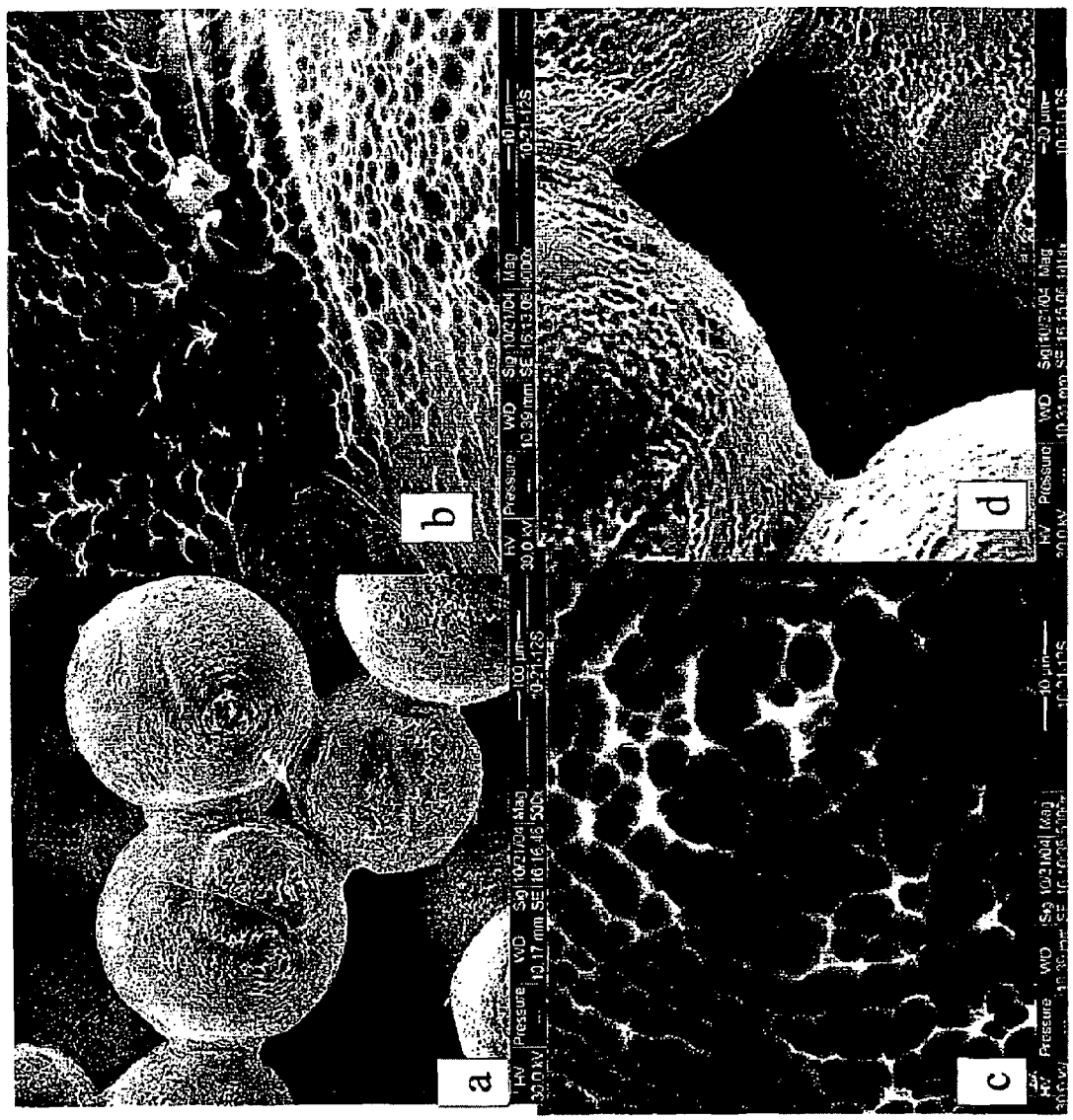
FIGS. 3A-D are a group of SEM micrographs of an etched surface of a cobalt-chromium porous coated stem implant at magnifications of 500× (FIG. 3A), 4000× (FIG. 3B), 5000× (FIG. 3C) and 1414× (FIG. 3D), which has been etched for 15 minutes at room temperature in accordance with one embodiment of the invention.
Figure 4:
FIGS. 4A-D are a group of SEM micrographs of an etched surface of a cobalt-chromium porous coated shoulder implant at magnifications of 811× (FIG. 4A), 4000× (FIG. 4B), 5000× (FIG. 4C) and 500× (FIG. 4D), which has been etched for 30 minutes at room temperature in accordance with one embodiment of the invention.
Figure 4:
Figure 4:
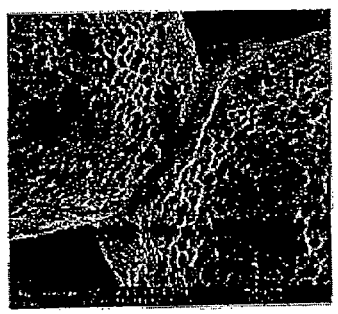
Figure 4:
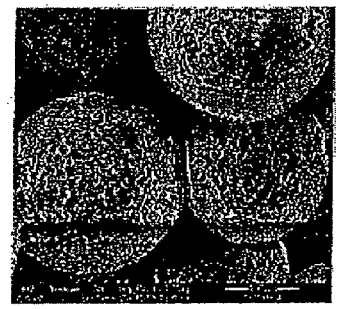
Figure 5:
FIGS. 5A-D are a group of SEM micrographs of an etched surface of a cobalt-chromium porous coated shoulder implant at magnifications of 500× (FIG. 5A), 4000× (FIG. 5B), 5000× (FIG. 5C) and 500× (FIG. 5D), which has been etched for 30 minutes at room temperature in accordance with one embodiment of the invention.
Figure 5:
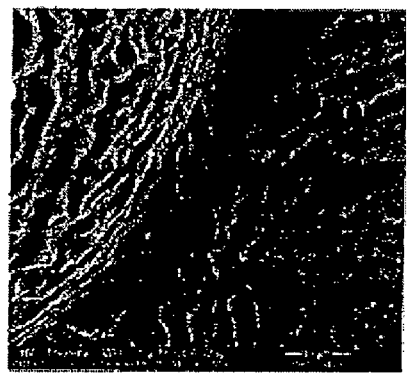
Figure 5:
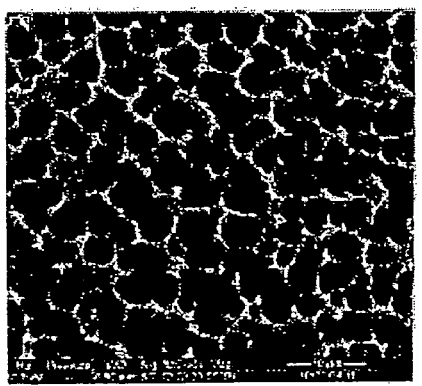
Figure 5:
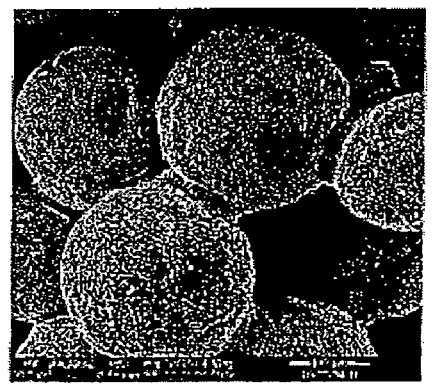
Figure 6:
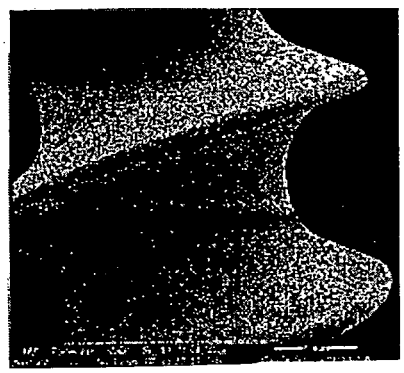
FIGS. 6A-D are a group of SEM micrographs of an etched surface of a cobalt-chromium screw at magnifications of 54× (FIG. 6A), 500× (FIG. 6B), 2000× (FIG. 6C) and 5000× (FIG. 6D), which has been etched for 30 minutes at room temperature in accordance with one embodiment of the invention.
Figure 6:
Figure 6:
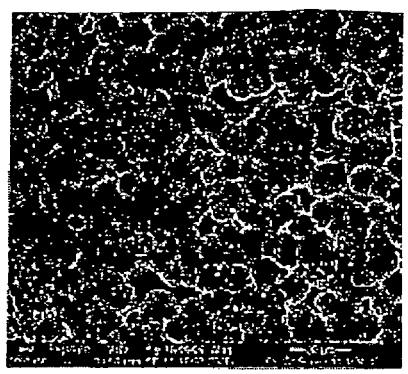
Figure 6:
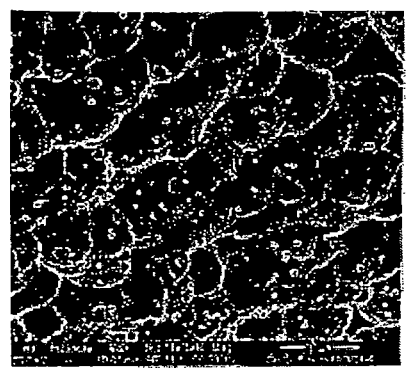

FIG. 2 is an SEM micrograph of an etched surface of a cobalt-chromium porous coated sample at a 5000× magnification which as been etched for 15 minutes at room temperature in an etching solution having 0.9M $NH_4Cl$, 4.6M HCl, 5.6M $H_3PO_4$, 20 ml $H_2O$, and 1.5M $H_2O_2$.

FIGS. 3A-D are a group of SEM micrographs of an etched surface of a cobalt-chromium porous coated stem implant. FIG. 3A shows the etched bead surface at 500× magnification, FIG. 3B shows that the bead connection at 4000× magnification is not over-etched, FIG. 3C shows the etching patterns at 5000× magnification and FIG. 3D shows the etching underneath bead surface at 1414× magnification. The implant has been etched for 15 minutes at room temperature in an etching solution having 4.6M HCl, 5.6M $H_3PO_4$, 1.5M $H_2O_2$, and 0.9M $NH_4Cl$.

FIGS. 4A-D are a group of SEM micrographs of an etched surface of a Co—Cr POROCOAT® porous coated shoulder implant. FIG. 4A shows the etched bead surface at 811× magnification, FIG. 4B shows that the bead connection at 4000× magnification is not over-etched, FIG. 4C shows the etching patterns at 5000× magnification and FIG. 4D shows the etching underneath bead surface at 500× magnification. The implant has been etched for 30 minutes at room temperature in an etching solution having 4.6M HCl, 5.6M $H_3PO_4$, 1.5M $H_2O_2$, and 0.9M $NH_4Cl$.

FIGS. 5A-D are a group of SEM micrographs of an etched surface of a Co—Cr POROCOAT® porous coated shoulder implant. FIG. 5A shows the etched bead surface at 500× magnification, FIG. 5B shows that the bead connection at 4000× magnification and it is not over-etched, FIG. 5C shows the etching patterns at 5000× magnification and FIG. 5D shows the etching on an underneath bead surface at 500× magnification. The implant has been etched for 30 minutes at room temperature in an etching solution having 4.6M HCl, 5.6M $H_3PO_4$, 1.5M $H_2O_2$, and 0.9M $NH_4Cl$.

FIGS. 6A-D are a group of SEM micrographs of an etched surface of a Co—Cr screw. FIGS. 6A, 6B, 6C and 6D are taken at a magnification of 54×, 500×, 2000× and 5000×, respectively. The implant has been etched for 30 minutes at room temperature in an etching solution having 4.6M HCl, 5.6M $H_3PO_4$, 0.7M $NH_4Cl$, and 0.4M $(NH_4)_2S_2O_8$.

Figure 7:
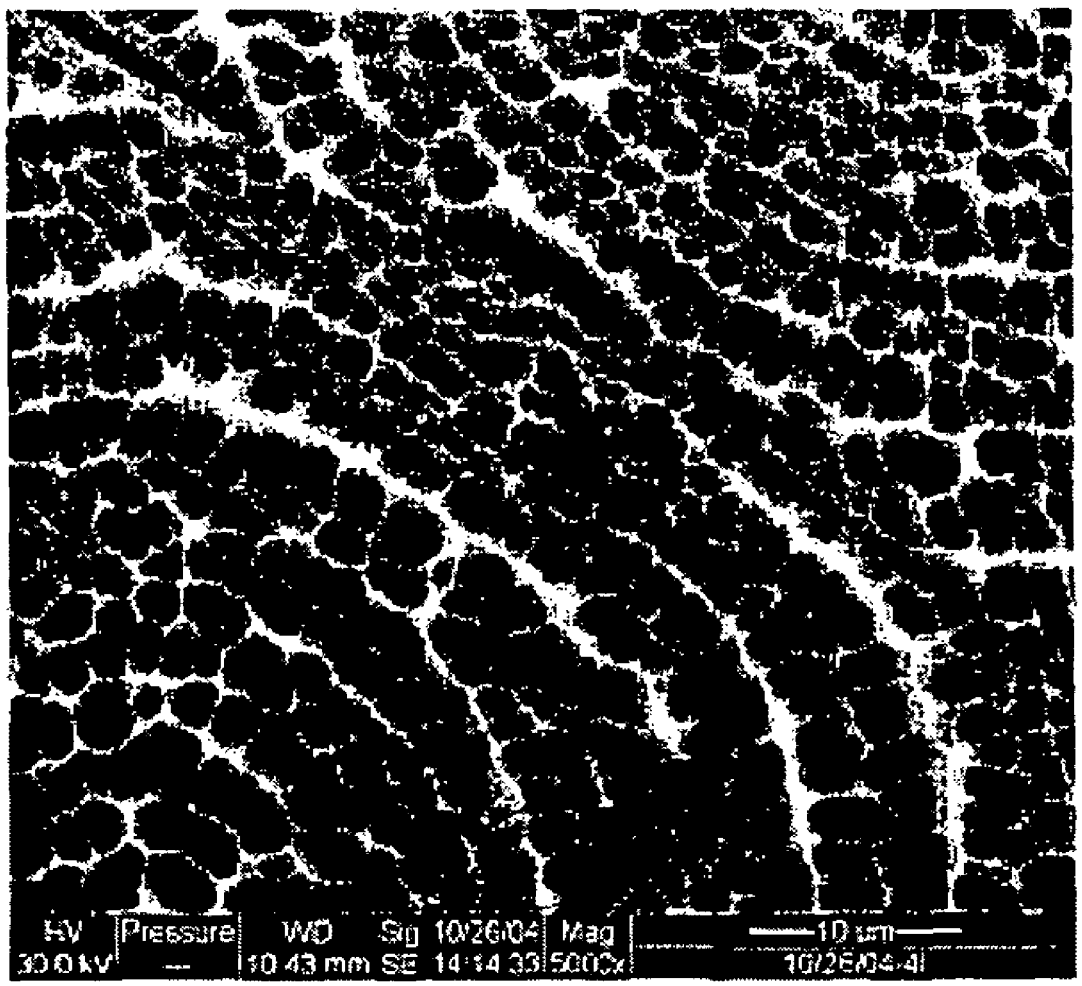
FIG. 7 is an SEM micrograph of an etched surface of a cobalt-chromium porous coated shoulder implant at a 5000× magnification which as been etched for 30 minutes at room temperature in accordance with one embodiment of the invention.

FIG. 7 is an SEM micrograph of an etched surface an etched Co—Cr POROCOAT® porous coated shoulder implant etched for 30 minutes at room temperature in an etching solution having 4.6M HCl, 5.6M $H_3PO_4$, and 0.58M $(NH_4)_2S_2O_8$.

Figure 8:
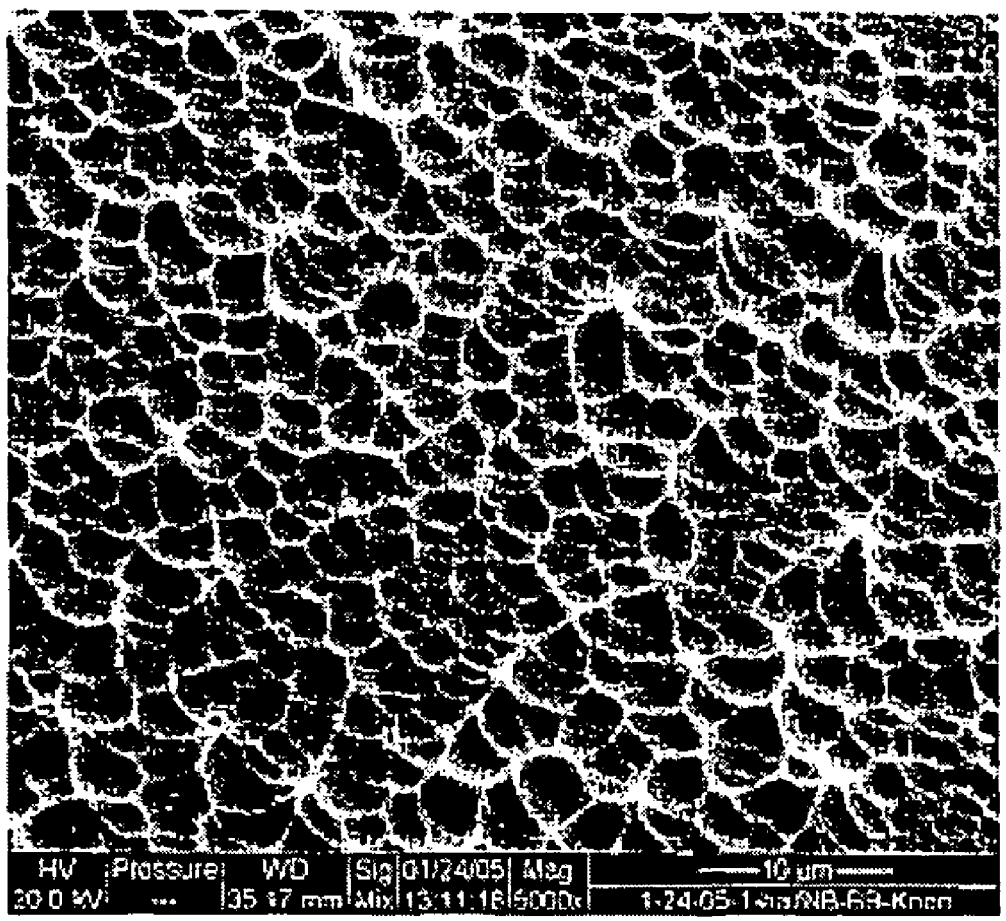
FIG. 8 is an SEM micrograph of an etched surface of a cobalt-chromium porous coated sample at a 5000× magnification which as been etched for 30 minutes at room temperature in accordance with one embodiment of the invention.

FIG. 8 is an SEM micrograph of an etched Co—Cr POROCOAT® porous coated sample etched for 30 minutes at room temperature in an etching solution having 4.6M HCl, 5.6M $H_3PO_4$, 0.7M $NH_4Cl$ and 0.3M $(NH_4)_2S_2O_8$.

Collectively, these results show that the etching solution of the invention provides a relatively mild etching solution that is able to achieve a uniform, nanometer and micrometer sized textured surface over the surface exposed to the etching solution. The time of exposure to the etching fluid may vary, although a uniformed textured surface can be produced with as little as four minutes of exposure. Thus, etching of an entire surface can be performed rapidly in a very short period of time.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed:

1. A chromium containing biomedical implant, comprising: a chromium containing metallic substrate including a textured surface with a plurality of indentations comprising depths in a range up to about 2.4 micrometers, the textured surface comprising a plurality of metallic elements and adhering on a surface of the metallic substrate to form a porous surface, the plurality of indentations being distributed on the plurality of metallic elements and the surface of the metallic substrate, wherein the plurality of indentations is produced by an etching solution comprising:

an acid selected from the group consisting of a hydrogen halide acid, and a mixture of a hydrogen halide acid and an oxyacid, wherein the hydrogen halide acid has a concentration in the range of about 1M to 12M, and the oxyacid has a concentration range of about 0.01M to 14M;

a chlorine containing compound at a concentration in the range of about 0.01M to 2M; and an oxidant at a concentration in the range of about 0.01M to 10M, the etching solution being free of hydrogen fluoride, the plurality of indentations having diameters in the range of about 200 nanometers to 15 micrometers.

2. The implant of claim 1, wherein the hydrogen halide acid is at a concentration in the range of about 3.5M to 8M.

3. The implant of claim 1, wherein the hydrogen halide acid is selected from the group consisting of hydrogen chloride, hydrogen bromide, and hydrogen iodide.

4. The implant of claim 1, wherein the oxyacid is at a concentration in the range of about 4M to 8M.

5. The implant of claim 1, wherein the oxyacid is at a concentration of about 5.6M.

6. The implant of claim 1, wherein the oxyacid is selected from the group consisting of phosphoric acid, nitric acid, and sulfuric acid.

7. The implant of claim 1, wherein the chlorine containing compound is at a concentration range of about 0.6M to 1.1 M.

8. The implant of claim 1, wherein the chlorine containing compound is selected from the consisting of sodium chloride, potassium chloride, calcium chloride, ammonium chloride, iron chloride and combinations thereof.

9. The implant of claim 1, wherein the etching solution further comprises a phosphate containing compound at a concentration in a range of about 0.01M to 0.4M.

10. The implant of claim 1, wherein the etching solution further comprises a phosphate containing compound selected from the group consisting of potassium phosphate, sodium phosphate, and sodium dihydrogen phosphate.

11. The implant of claim 1, wherein the oxidant is at a concentration range of about 0.08M to 3.4M.

12. The implant of claim 1, wherein the oxidant is at a concentration range of about 0.5M to 1.6M.

13. The implant of claim 1, wherein the oxidant is selected from the group consisting of hydrogen peroxide and sodium dihydrogen phosphate.

14. The implant of claim 1, wherein the chromium containing implant is made of a cobalt-chromium alloy.

15. The implant of claim 1, wherein the chromium containing implant further comprises a coating.

16. The implant of claim 15, wherein the coating is a ceramic coating.

17. The implant of claim 1, wherein the plurality of indentations is produced by exposing the implant to the etching fluid at a temperature in the range of about 10° C. to 100° C.

18. The implant of claim 1, wherein the plurality of indentations is produced by exposing the implant to the etching fluid at a temperature in the range of about 20° C. to 25° C.

19. The implant of claim 1, wherein the plurality of indentations is produced by exposing the implant to the etching fluid for an etching time in the range of about 3 minutes to 60 minutes.

20. The implant of claim 1, wherein the plurality of indentations is produced by exposing the implant to the etching fluid for an etching time in the range of about 15 minutes to 30 minutes.

21. The implant of claim 1, wherein the metallic elements comprise at least one of metallic particles, metallic fibers, and metallic wires.

22. The implant of claim 21, wherein the metallic elements comprise cobalt-chromium alloy elements.

23. The implant of claim 1, wherein the plurality of metallic elements comprises a metallic element having a size from about 40 microns to 10 millimeters.

24. The implant of claim 1, wherein the plurality of metallic elements comprises at least one of metallic beads and metallic wires.

25. The implant of claim 1, wherein the oxidant includes at least one of peroxides, nitrites, perchlorates, chlorates, chlorites, hypochlorites, dichromates, permanganates, and persulphates.

26. The implant of claim 25, wherein the oxidant includes ammonium persulfate.

27. The implant of claim 25, wherein the hydrogen halide acid is hydrochloric acid.

* * * * *

UNITED STATES PATENT AND TRADEMARK OFFICE
CERTIFICATE OF CORRECTION

PATENT NO. : 7,901,462 B2  
APPLICATION NO. : 11/165209  
DATED : March 8, 2011  
INVENTOR(S) : Xiaofan Yang et al.

Page 1 of 1

It is certified that error appears in the above-identified patent and that said Letters Patent is hereby corrected as shown below:

Col. 11, claim 8, line 11, after "the" insert --group--.

Signed and Sealed this  
Fourteenth Day of June, 2011

David J. Kappos  
*Director of the United States Patent and Trademark Office*